(12) United States Patent
Yusoff et al.

(10) Patent No.: US 8,883,480 B2
(45) Date of Patent: Nov. 11, 2014

(54) ANTIVIRAL PEPTIDE AGAINST AVIAN INFLUENZA VIRUS H9N2

(75) Inventors: Khatijah Mohd Yusoff, Serdang (MY); Abdul Rahman Omar, Serdang (MY); Aini Ideris, Serdang (MY); Mohamed Rajik, Serdang (MY)

(73) Assignee: Universiti Putra Malaysia, Serdang, Selangor Darul Ehsan (MY)

( * ) Notice: Subject to any disclaimer, the term of this patent is extended or adjusted under 35 U.S.C. 154(b) by 723 days.

(21) Appl. No.: 12/995,889

(22) PCT Filed: Jun. 10, 2009

(86) PCT No.: PCT/MY2009/000071
§ 371 (c)(1), (2), (4) Date: Dec. 2, 2010

(87) PCT Pub. No.: WO2009/151313
PCT Pub. Date: Dec. 17, 2009

(65) Prior Publication Data
US 2011/0135676 A1  Jun. 9, 2011

(30) Foreign Application Priority Data
Jun. 12, 2008 (MY) .................................. 20082061

(51) Int. Cl.
| C12N 7/00 | (2006.01) |
| A61K 39/00 | (2006.01) |
| C12N 15/00 | (2006.01) |
| C07K 16/10 | (2006.01) |
| C07K 7/06 | (2006.01) |
| C07K 14/005 | (2006.01) |
| A61K 38/00 | (2006.01) |

(52) U.S. Cl.
CPC ........... C07K 14/005 (2013.01); C07K 16/1018 (2013.01); C12N 2760/16151 (2013.01); C07K 7/06 (2013.01); A61K 38/00 (2013.01); C12N 2760/16122 (2013.01); C12N 7/00 (2013.01)
USPC ................... 435/235.1; 424/184.1; 435/320.1

(58) Field of Classification Search
USPC ........................................................... 435/5
See application file for complete search history.

(56) References Cited

U.S. PATENT DOCUMENTS 7,208,293 B2 * 4/2007 Ladner et al. ................ 435/69.7

FOREIGN PATENT DOCUMENTS

| WO | WO2007022425 | * | 2/2007 |
| WO | WO 2008/157419 | | 12/2008 |

OTHER PUBLICATIONS

Zhizhou et al., Bing du Xue bao, 2007, english translation abstract PDF.*
Desogus et al., Production and characterization of a human recombinant monoclonal Fab Fragment Specific for Influenza A Viruses, 2003, Clinical and Diagnostic Laboratory Immunology, 10(4):680-685.*
Kuang, Z. et al., "Screening of Peptides as Broad-spectrum Neuraminidase Inhibitors against Influenza Viruses," Bing du Xue bao, 2007, vol. 23(3), pp. 165-171. (English translation of abstract).
Song, H. et al., "Identification of peptide mimotopes of an abroad-spectrum neutralizing epitope of highly pathogenic avian influenza hemagglutinin," Bing du Xue bao. Nov. 2008, vol. 24(6), pp. 421-426. (English translation of abstract).
Rajik, M. et al., "Identification and characterisation of a novel antiviral peptide against avian influenza virus H9N2," Virology Journal, Jun. 5, 2009, vol. 6(74), pp. 1-12.
Rajik, M. et al., "A novel peptide inhibits the influenza virus replication by preventing the viral attachment to the host cells," International Journal of Biological Sciences, Aug. 8, 2009, vol. 5(6), pp. 543-548.

* cited by examiner

Primary Examiner — Stacy B. Chen
Assistant Examiner — Barry A Chestnut
(74) Attorney, Agent, or Firm — Preti Flaherty Beliveau & Pachios LLP

(57) ABSTRACT

The present invention relates to recombinant phages carrying fusion peptides that bind to avian influenza virus (AIV). Such phages are useful as diagnostic reagents to replace anti-AIV antibodies because the phages are capable of competing with the latter antibodies for binding sites on the virus. Synthetic peptides with the sequence CNDFRSKTC, either in linear or cyclic conformations, or fusion phages bearing the above said peptides inhibited AIV propagation in embryonated egg as well as in MDCK cell lines. Therefore they may be used as'therapeutic agents to control, to treat and to eradicate bird flu caused by avian influenza virus.

4 Claims, 5 Drawing Sheets

Series 1: FP-P1 phage
Series 2: FP-P1 phage with polyclonal antibodies

Series 1: Cyclic peptide [CNDFRSKTC]
Series 2: Linear peptide [NDFRSKT]
Series 3: Control [CSWGEYDMC]

Series 1: Fusion phage (FP-P1)
Series 2: Control (Wild Phage M13)

Series 1: Fusion Phage (FP-P1)
Series 2: Control (Wild phage M13)

Series 1: Fusion Phage (FP-P1)
Series 2: Control (Wild phage M13)

ANTIVIRAL PEPTIDE AGAINST AVIAN INFLUENZA VIRUS H9N2

1.0 FIELD OF INVENTION

The present invention relates to a novel antiviral peptide and a fusion phage which acts against Avian Influenza Virus (MV) subtype H9N2. More specifically, the fusion phage displays the sequence CNDFRSKTC (SEQ ID NO:1) on its surface protein $P_3$ which binds to MV H9N2 with an $IC_{50}$ value of less $10^{13}$ pfu/100 µl. Synthetic peptides with amino acid sequence CNDFRSKTC, either in linear or cyclic conformations, inhibited the propagation of AIV H9N2 with an $IC_{50}$ value less than about 100 µM

2.0 BACKGROUND OF INVENTION

Avian influenza virus (AIV) belongs to the family of Orthomyxoviridae which contains two genera, influenza A & B and influenza C (Lamb and Krug, 1996). These viruses are the major cause of morbidity and mortality among poultries in the world. It is the causative agent of the most dangerous disease, called bird flu in common terms (Webster et al., 1992). Although these viruses do not infect humans, several instances of human infections and outbreaks have been reported (CDC, 2008; Normile, 2004; Parry, 2004). Influenza A viruses are enveloped with lipid bilayer and contain eight single-stranded, segmented, negative sense RNAs. There are two glycoproteins present on the surface of the virions namely, haemagglutinin (HA) and neurammidase (NA), and one ion channel protein (M2). The glycoproteins are the major antigenic determinants of influenza viruses. The HA protein initiates the first step in the viral infection, which involves the attachment of viruses to the host cell surface sialic acid receptors (Lamb and Krug, 1996). The NA protein participates in the release of mature virions from the host cells (Palese of al., 1974). Therefore, in order to study the virus-host interaction and also to identify molecules that inhibit this process a bacteriophage displaying a specific peptide sequence was selected by its affinity to avian influenza virus strain H9N2 using a phage display library.

The preferred primary strategy for the prevention of influenza virus infection is annual vaccination among susceptible population. But the antiviral drugs play an important role in a comprehensive approach to control the illness and transmission (Hayden, 2006). There are two classes of antiviral drugs that have been approved for the treatment and prophylaxis. They are adamantane derivatives (amantadine and rimantadine) and neuraminidase inhibitors (NAIs; zanarnivir and oseltarnivir) (Nicholson et al., 2003). These adamantane derivatives act by binding and blocking the function of influenza A virus M2 ion channel protein and thereby prevents the viral replication inside the host cell (Wang et al., 1993)). Due to single point mutations in M2 proteins, adamantane resistant strains have emerged (Hay et al., 1986). These resistant viruses are typically fully pathogenic and transmissible (Hayden, 2006). The NAN inhibit the enzymatic activity of the neuraminidase protein and prevents viral release from the infected host cell. But NAI resistant strains have also emerged due to the mutations in the active site of the NA (Nicholson et al., 2003). The increasing resistance by the influenza A viruses against the both types of drugs highlights our necessity to identify novel drugs.

Traditionally, compounds from natural products obtained from plants, marine organisms, fungi or other microorganisms are used to identify antimicrobial or antiviral agents. Recently, combinatorial peptide libraries like phage display library are increasingly being used to identify peptide compounds for the same purpose (Doorbar et al., 1994). The broad structural diversity of peptides displayed on bacteriophages has made the phage display library an important tool to study proteinprotein interactions, especially in the identification of specific ligands that interact with a particular target (Devlin et al., 1990). Compounds that interact with target molecules are selected from phage libraries and screening processes are then used to identify lead compounds that have functional effects on the target. These lead compounds are then optimized for their activity and then the candidate drugs enter into clinical trials.

We used a cyclic peptide phage display library to identify peptide molecule that interacts with the influenza A virus H9N2 and proved its antiviral property in vitro and in ovo.

3.0 SUMMARY OF THE INVENTION

Accordingly it is an object of the present invention to provide for novel peptides and fusion phages that has antiviral activity against avian influenza virus A H9N2.

It is another object of the present invention to provide for a pharmaceutical composition containing a recombinant phage or a synthetic peptide according to the invention.

It is yet another object of the present invention to provide a diagnostic reagent containing a recombinant phage or a synthetic peptide according to the invention.

These objectives are accomplished by,

An isolated and purified recombinant phage bearing a fusion peptide or synthetic peptides derived from the fusion phage that binds to avian influenza virus A H9N2 and inhibits the propagation of the virus.

To identify a novel antiviral molecule, a population of recombinant phages displaying random disulfide constrained heptapeptide sequences was screened against the virus. Then the peptide displayed on the surface of the fusion phage was synthesized chemically. The isolated peptide has the sequence of NDFRSKT (SEQ ID NO:2) with an IC50 value of less than 100 ~M The specificity of the recombinant phage against the influenza virus A H9N2 was proved by an antibody—phage competition assay, in which the phages were able to compete with polyclonal antibodies for binding site on the viral surface proteins.

In the present invention, synthetic peptides based upon one of the isolated sequences, either in linear or cyclic conformation, such as the synthetic peptide CNDFRSKTC (SEQ ID NO:1), are able to inhibit the propagation of NDV, thereby preventing disease and spread of infection.

4.0 BRIEF DESCRIPTION OF THE FIGURES AND TABLE

Table I shows the heptapeptide sequences obtained from three rounds of biopanning against AIV H9N2.

Table 2 shows haernagglutination inhibition activities of synthetic peptides and fusion phages.

Figure I shows the results of the competition between recombinant phages bearing specific heptapeptide sequence and polyclonal antibodies for AIV H9N2.

5.0 DETAILED DESCRIPTION OF THE TABLES AND FIGURES

Table I shows the heptapeptide sequences obtained from four rounds of biopanning against AIV. After 4 rounds of selection and amplification 20, 35 and 35 individual clones from the $2^{nd}$, $3^{rd}$ and $4^{th}$ rounds, respectively, were sequenced.

Table 2 shows the inhibitory ability of the cyclic and linear peptides against the haernaggluti nation activity of the avian influenza virus H9N2. Experiments were performed in triplicates. + in the presence of, − in the absence of.

Figure I shows the results of the competition between recombinant phages bearing specific heptapeptide sequence and polyclonal antibodies for AIV. The polyclonal antibodies (pAb) inhibited the association of the fusion phage with AIV, suggesting that the phages may share some common binding sites with the antibody. Experiments were done in triplicates and the error bars represent the standard deviation of the mean. Series I—Fusion phage; Series 2—Fusion phage with polyclonal Antibodies.

Figure 1:
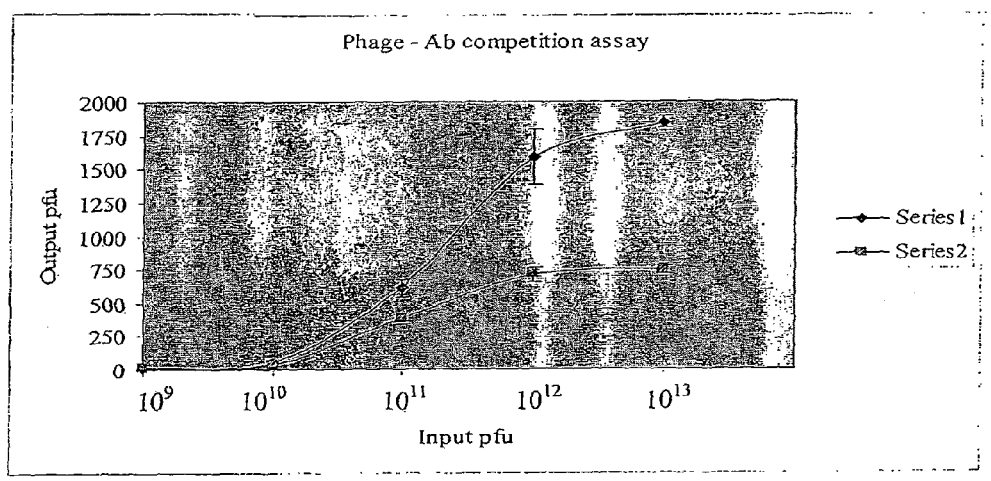
Figure 2:
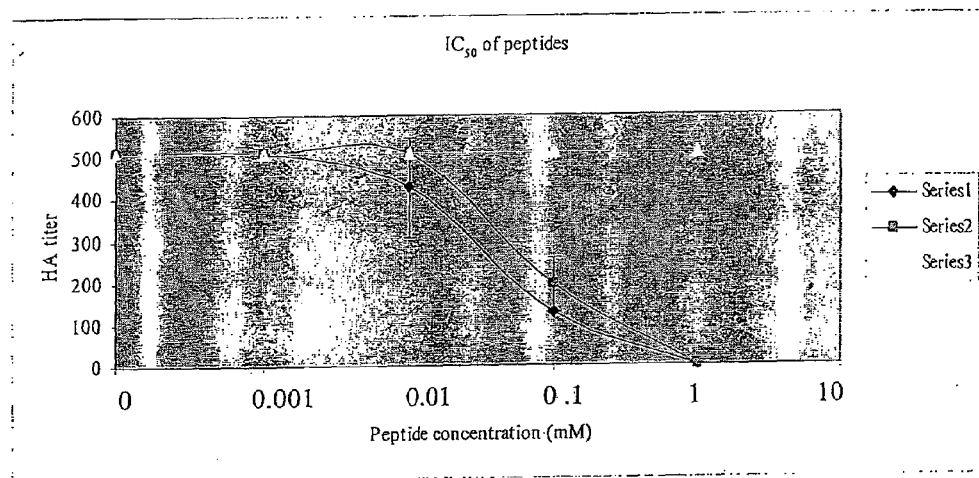
FIG. 2 shows the inhibition of MV propagation with synthetic peptides in ovo with Series 1: Cyclic peptide [CNDFRSKTC (SEQ ID NO:1)], Series 2: Linear peptide [NDFRSKT (SEQ ID NO:2)], and Series 3: Control [CSWGEYDMC (SEQ ID NO: 10)].

FIG. 2 shows the results of determination of the IC50 values of the synthetic peptides in ovo against AIV H9N2 propagation. Peptide concentration needed to inhibit 50% of the virus growth was determined using different concentrations of peptides. Experiments were done in triplicates and the error bars represent the standard deviation of the mean.

Figure 3:
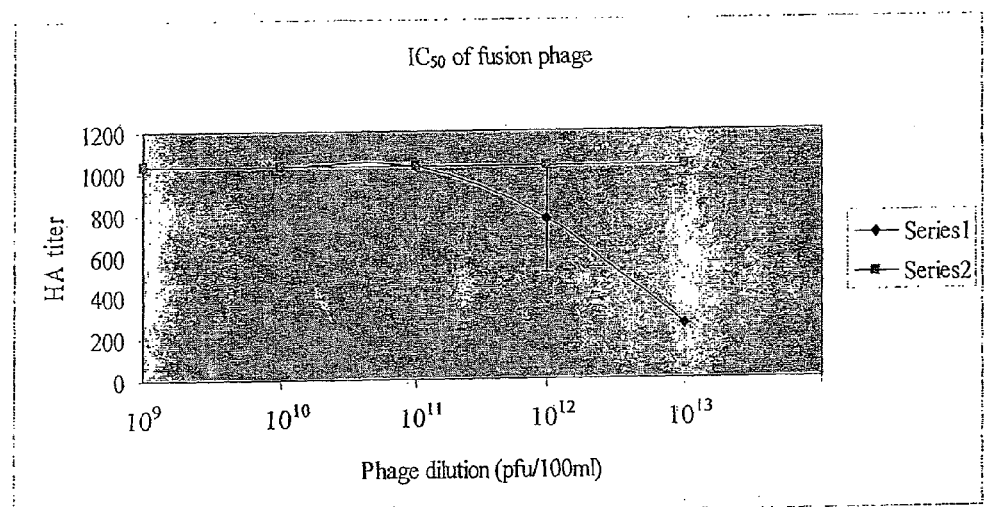
FIG. 3 shows the inhibition of AIV propagation with fusion phages in ovo.

FIG. 3 shows the results Of $IC_{50}$ values of fusion phage FP-P1 against AIV H9N2 virus propagation in ovo. Experiments were done in triplicates and the error bars represent the standard deviation of the mean. Series I—Fusion phage FP-Pl; Series 2—Wild phage as control.

Figure 4:
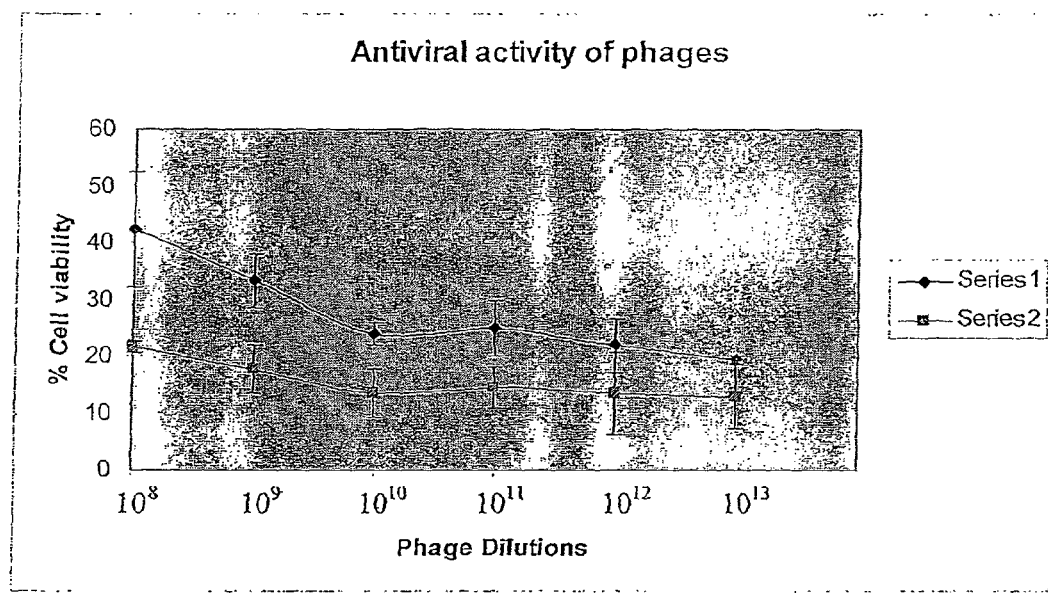
FIG. 4 shows the inhibition of AIV propagation with fusion phages in vitro.

FIG. 4 shows the results of antiviral activity of the fusion phage FP-P1 in vitro. Experiments were done in triplicates and the error bars represent the standard deviation of the mean. Series I—FP-P1; Series 2—Wild Phage M 13 as control.

Figure 5:
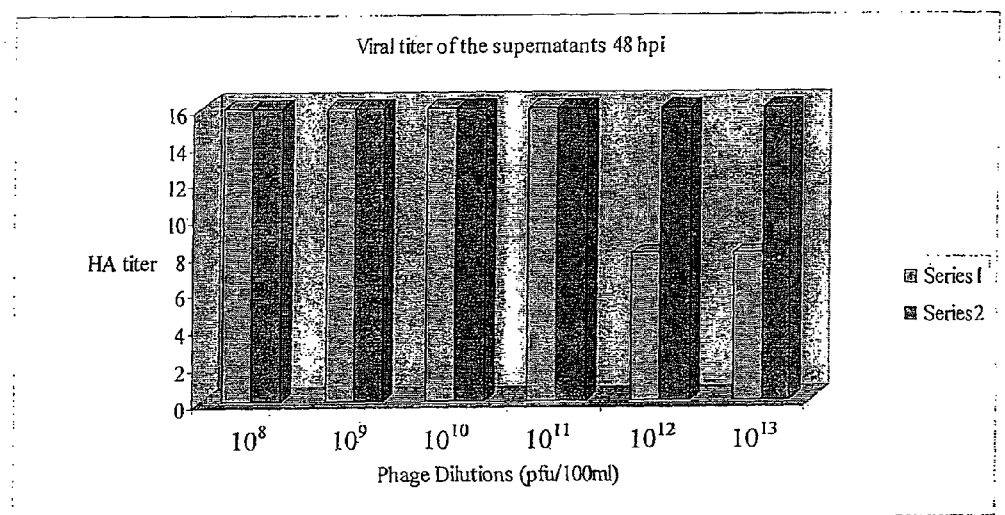
FIG. 5 shows the effect of fusion phage on viral replication in vitro.

FIG. 5 shows the results of the effect of the fusion phage FP-P1 on viral replication. MDCK cells were inoculated with untreated (o value) or FP-P I treated virus, and viral titers were determined on supernatants 72 hpi. Series I—FP-Pl; Series 2—Wild phage M 13 as control.

6.0 DETAILED DESCRIPTION OF THE INVENTION

The description described herein will be more fully understood with the following detailed description which is divided into different sections. Materials and methods employed in this invention are set forth in Examples. Examples 1 to 5 are the conventional materials and methods which are prerequisites of the invention.

Principles of Phage Display Technology

In phage display technology, random peptides are usually displayed on the surface of bacteriophage molecules as fusion protein by inserting synthetic oligonucleotides in the gene encoding the coat proteins. A collection of these recombinant phages are known as phage display library, allows the screening of vast numbers of peptide sequences against a target by an in vitro selection procedure known as biopanning (Parmley et al., 1988 and Smith et al., 1993). In the present invention, the target used was whole AIV H9N2 virus particles and the library employed was the disulfide constrained library obtained from New England Biolabs, Inc. In this particular library, the displayed peptide molecules are flanked by a cysteine residue to the gpIII protein of phage M13. The cysteine residues help the peptides to attain a fixed cyclic shape, in the absence of reducing agents. This disulfide constrained library useful for targets whose interacting components (native ligands) have discontinuous binding sites (conformational epitope) (Hoess et al., 1994); in which amino acids are brought from different positions in a polypeptide to form an essential contact area. Besides, the disulfide constrained cyclic peptide library is more useful in selecting high affinity ligands rather than a linear peptide library (O'Neil et aL, 1992; Gho et al., 1997).

Affinity Selection of Peptides that Bind to AIV

The avian influenza virus contains two surface glycoproteins namely haernagglutinin (HA) and neuraminidase (NA) which is responsible for virus entry and exit into and from the host cell. We therefore decided to employ the disulfide constrained library against the whole virus particles to select for conformational ligands which bind the surface proteins. Figure I summarizes the major steps involved in the selection of these ligands. First, the whole virus particles were directly attached to the surface of a high binding microliter plate well. The library was then added into the well to allow the recombinant phage particles to bind with the virus particles. The unbound phages were washed out and the bound phages were eluted at low pH. The eluted phages were then amplified in the bacterium, *Escherichia coli* and the amplified phages were used in second round of biopanning. This procedure was repeated for four times. After four successive rounds of affinity selection and amplification, a subset of the selected phages was grown up individually and tile identity of the peptides that bind to core particles were obtained by sequencing tile gpIII gene carrying the insertion.

In order to select high affinity binding phages, the stringency of selection was increased by (i) performing the biopanning at room temperature (28'C), (1i) shortening the time of binding to I h to select for ligands with rapid on rates (Ko,), (iii) washing the wells thoroughly (10 times) to remove low affinity binding phages, and (iv) repeating 4 rounds of biopanning to enrich high affinity binding clones. 47% of phages analysed from the fourth round panning carried the fusion peptide sequence NDFRSKT (SEQ ID NO:2), 10.5% containing QHSTKWF (SEQ ID NO:3) motif followed by LPYAAKH (SEQ ID NO:4) and ILGDKVG (SEQ ID NO:5), 5% each and other unrelated sequences (Table 1). Streptavidin target was used for positive control which gave a consensus motif of HPQ sequence in all clones, which in good agreement with that reported by Devlin et al. (1990). No recognizable consensus sequence was observed with bovine serum albumin (BSA), which was used as negative control.

As used herein, the term "fusion peptide" refers to amino acid sequence genetically encoded by a bacteriophage and physically linked to a coat protein of the phage. The claimed fusion peptides contain amino acid sequences NDFRSKT, but it is not limited to: (i) amino acid sequence which is shorter or longer than the claimed amino acid sequences; (ii) variations in the amino acid sequences, particularly amino acid substitutions within the same category as described below; (iii) amino acid sequences sharing at least 60% homology with those of the claimed fusion peptides and; (iv) either linear or constrained conformation.

AIV possesses two surface glycoproteins, HA and NA, which protrude from the viral lipid bilayer membrane. These glycoproteins are essential for the entry and release of viruses into and outside of the host cells respectively. Since the phages bearing the sequences NDFRSKT bound to the virion in solution, these sequences may, to a certain extent, resemble a region on the host cell receptor that interacts with the intact virion.

Phages Compete with Antibody for Binding Sites on AIV

The surface glycoproteins HA and NA are two important proteins that elicit antibody production in the host. In a phage-antibody competition assay, the phages were able to bind to one of the mimotopes and therefore inhibit the binding of antibodies raised against the virion. Figure I shows that the recombinant phages displaying the peptide NDFRSKT, selected from biopanning experiment, were able to compete with the antibodies for the binding site on AIV. In the presence of the antibody, the number of phages bound to the virus coated wells reduced dramatically as a result of competition between these two molecules for the same binding site on the virus. Thus the recombinant phage molecules may serve as a potential diagnostic agent for the AIV infection.

Antiviral Activity of Synthetic Peptides and Fusion Phages in Ovo

AIV can easily be propagated in the allantoic fluid of embryonated chicken eggs. Therefore, the virus and the propagation system provide a simple model to assess directly the antiviral activities of a particular compound or peptide in vivo. The amount of virus present in the allantoic fluids, before and after the antiviral compounds treatment, is determined by haernagglutination titer. Injection of the claimed peptide either in cyclic or linear form and the fusion phage displaying the peptide reduced the AIV titer in the allantoic fluid (FIGS. 2 and 3). The cyclic peptide showed higher $IC_{50}$ value at a peptide concentration lower than 100 μM to the linear peptide. Furthermore, cyclization can avoid the digestion of the peptides by exopeptidases. Thus the synthetic peptides claimed herein can be used as therapeutic agents to treat, control and also to eradicate the disease.

Antiviral Activity of Fusion Phages In Vitro

MDCK cell lines are effective medium for the propagation of avian influenza viruses in vitro. The in vitro antiviral property of the fusion phages against the virus multiplication were checked in these cell lines. The inhibition of viral replication was indirectly checked by the cell viability, before and after the treatment with the fusion phage molecules. The cell viability increases nearly 2 fold after the infection with phage treated viruses to the untreated viruses (FIG. 4). The reduction in viral titer was further confirmed by haemagglutination test of the supernatants (FIG. 5). This experiment proved the antiviral property of the fusion phage molecules in vitro.

EXAMPLES

Example 1

Propagation and Purification of AIV

The propagation and purification methods were adapted and modified from Blaskovic and Styk (1967) and Yusoff et al. (1996), respectively. AIV subtype H9N2 was injected into a 9 days old specific pathogen free embryonated chicken eggs. After 3 days of incubation at 37° C., the allantoic fluid was harvested and clarified by centrifugation (30 min, 35,000×g, 4° C. The virus was purified from the clarified supernatants by 30%-60% sucrose gradient ultracentrifugation (3.5 h, 285,000×g, 4° C. and was used for the studies below.

Example 2

Biopanning of Purified AIV

The protein concentration of virus was measured using the Bradford assay (1976). AIV (15 μg/ml) was coated onto a microtiter plate well [$Na_2CO_3$/$NaHCO_3$ buffer (0.1 M, pH 9.6)]. Streptavidin and BSA were used as positive and negative controls respectively. The experiment was carried out at room temperature (about 25° C.). Phages from a disulfide constrained 7-mer phage display library (New England Biolabs, USA) were diluted to I×$10^{11}$ pfu in TBS [50 mM Tris-HCl (pH 7.5), 150 mM NaCl; 110 μl] and added into each coated well. The mixtures were incubated for 30 min. The wells were washed with TBST JBS+0.1% v/v Tween-20). Bound phages were eluted with glycine-HCl [ 0.1 M, (pH 2.2); 100 μl] by rocking gently for 7-8 min and neutralized with Tris-HCl [I M, (pH 9); 115 μl. The output pfu was determined by titrating the eluate (10 μl) while the remainder eluate was amplified in *E. coli* stain ER2738 (F' Iacl$^q$ Δ(IacZ) M]5proA$^+$B$^+$ zzf::TnI0(Tet$^R$)/fhuA2supE thi Δ(lac-proAB) Δ(hsdMS-mcrB)5 ($r_k$-$m_k$-McrBC-)} at 37° C., shaking for 5 hr. The panning process was repeated for a further 3 rounds.

Example 3

Phage Titration

Phage titration method was adapted from Sambrook et al. (1989).

Example 4

Sequencing of the Selected Phages

Single plaques from all 4 rounds of panning were picked from (Luria Broth) LB plates (used in output titration) and grown in LB media. Single stranded DNA of the phages was extracted as described by Sambrook et al, (1989). Sequencing of inserts was done using the ABI automated sequencer by First Base Laboratories Sdn Bhd, Kuala lumpur.

Example 5

Antibody Competition Assay

Wells were coated with AIV (15 μg/ml) and polyclonal antibodies (1:500 dilution; 100 μl) raised against AIV were added with a series of different phage concentrations ($10^9$-$10^{13}$ pfu; 100 μl). The mixtures were incubated for 1 hour and washed 6× with Tris-buffered saline—Tween (TBST). Bound phages were eluted and titered as described above.

Example 6

Determination of $IC_{50}$ of Peptides and Fusion Phages in the Inhibition of AIV Propagation in Ovo Nine-day-old embryonated chicken eggs were inoculated with 100 μl of AIV (8 HA units) and an equal volume of different concentrations of peptide (0.1 μM-I mM) or fusion phages ($10^8$-$10^{13}$ pfu). The eggs were incubated at 37° C. Three eggs were used for each peptide concentration. For the positive control, only AIV was inoculated and for the negative control, the virus was substituted by peptides or phages. Peptides (100 μl) were injected into appropriate eggs daily for another 3 days. A day after the 4$^{th}$ injection, the eggs were chilled overnight and the allantoic fluid was harvested. The haemagglutination activities of the allantoic fluid samples were then determined according to Grace et al, (1973).

Example 7

Determination of $IC_{50}$ of Fusion Phages in the Inhibition of AIV Propagation In Vitro MDCK cells were inoculated with medium alone or phage treated ($10^8$-$10^{13}$ pfu/100 μl) or non-treated virus (multiplicity of infection [MoI] 0.05) for I hr at 37° C. Following adsorption, monolayers were washed and incubated in EMEM containing 5% fetal bovine serum (FBS). Cytopathic effect was monitored by light microscopy and quantitated by XTT Cell Viability Assay Kit (Biotium, USA). To assess viral replication, MDCK cells were inoculated with phage-treated or untreated virus at an MoI of 0.05, supernatants were collected at 72 hpi, and viral titers were determined by HA titer. The $IC_{50}$ value was estimated by interpolation of the dose-response curve.

Although the invention has been described above with respect to various presently preferred embodiments, it will be apparent to one of ordinary skill in the art that many variations and modifications may be made. Therefore, the invention is not to be understood as limited to the particular embodiments presented herein but, rather, is to be understood as embracing all such variations and modifications which fall within the scope of the claims appended hereto.

All references disclosed herein are incorporated by reference in their entirety.

TABLE 1

| Rounds of panning | Heptapeptide sequences | Frequency of sequences (%) |
|---|---|---|
| $2^{nd}$ round | Unrelated sequences | 100 |
| $3^{rd}$ round | LPYAAKH (SEQ ID NO: 5)/ LPYGSKH (SEQ ID NO: 6) | 25 |
|  | ILGYKVG (SEQ ID NO: 7) | 17 |
|  | Unrelated sequences | 58 |

TABLE 1-continued

| Rounds of panning | Heptapeptide sequences | Frequency of sequences (%) |
|---|---|---|
| $4^{th}$ round | NDFRSKT (SEQ ID NO: 2) | 47 |
|  | QHSTKWF (SEQ ID NO: 4) | 10.5 |
|  | LPYAAKH (SEQ ID NO: 5) | 5 |
|  | ILGDKVG (SEQ ID NO: 6) | 5 |
|  | Unrelated sequences | 23 |
| $3^{rd}$ round Streptavidin | HPQFLSL (SEQ ID NO: 8) | 55 |
|  | GLYNHPQ (SEQ ID NO: 9) | 27 |
|  | Unrelated sequences | 18 |

TABLE 2

| Peptide concentration (mM; 50 µl)/Phage Particles | Agglutination of RBC (+AIV 32 HAU; 50 µl) | Agglutination of RBC (−AIV 32 HAU; 50 µl) |
|---|---|---|
| Cyclic 1.0 | No | No |
| Cyclic 0.1 | No | No |
| Cyclic 0.01 | Yes | No |
| Cyclic 0 | Yes | No |
| Linear 1.0 | No | No |
| Linear 0.1 | No | No |
| Linear 0.01 | Yes | No |
| Linear 0 | Yes | No |
| Phage ($10^{13}$ pfu/100 µl) | No | No |
| Phage ($10^{12}$ pfu/100 µl) | Yes | No |

What is claimed is:

1. An isolated and purified recombinant phage bearing a fusion peptide, wherein the fusion peptide is the amino acid of sequence NDFRSKT SEQ ID NO:2.

2. A method for inhibiting avian influenza virus H9N2 in an individual wherein said individual is an avian comprising administering to said individual an inhibitory amount of a recombinant phage according to claim 1.

3. A composition for inhibiting propagation of the Avian influenza virus containing a recombinant phage as claimed in claim 1.

4. A diagnostic reagent containing a recombinant phage as claimed in claim 1.

* * * * *

SEQUENCE LISTING

<160> NUMBER OF SEQ ID NOS: 10

<210> SEQ ID NO 1
<211> LENGTH: 9
<212> TYPE: PRT
<213> ORGANISM: Artificial sequence
<220> FEATURE:
<223> OTHER INFORMATION: Derived from avian influenza virus H9N2

<400> SEQUENCE: 1

Cys Asn Asp Phe Arg Ser Lys Thr Cys
1               5

<210> SEQ ID NO 2
<211> LENGTH: 7
<212> TYPE: PRT
<213> ORGANISM: Artificial sequence
<220> FEATURE:
<223> OTHER INFORMATION: Derived from avian influenza virus H9N2

<400> SEQUENCE: 2

Asn Asp Phe Arg Ser Lys Thr
1               5

<210> SEQ ID NO 3
<211> LENGTH: 7
<212> TYPE: PRT
<213> ORGANISM: Artificial sequence
<220> FEATURE:
<223> OTHER INFORMATION: Peptide derived from avian influenza virus H9N2

<400> SEQUENCE: 3

Gln His Ser Thr Lys Trp Phe
1               5

```
<210> SEQ ID NO 4
<211> LENGTH: 7
<212> TYPE: PRT
<213> ORGANISM: Artificial sequence
<220> FEATURE:
<223> OTHER INFORMATION: Derived from avian influenza virus H9N2

<400> SEQUENCE: 4

Leu Pro Tyr Ala Ala Lys His
1               5

<210> SEQ ID NO 5
<211> LENGTH: 7
<212> TYPE: PRT
<213> ORGANISM: Artificial sequence
<220> FEATURE:
<223> OTHER INFORMATION: Derived from avian influenza virus H9N2

<400> SEQUENCE: 5

Ile Leu Gly Asp Lys Val Gly
1               5

<210> SEQ ID NO 6
<211> LENGTH: 7
<212> TYPE: PRT
<213> ORGANISM: Artificial sequence
<220> FEATURE:
<223> OTHER INFORMATION: Derived from avian influenza virus H9N2

<400> SEQUENCE: 6

Leu Pro Tyr Gly Ser Lys His
1               5

<210> SEQ ID NO 7
<211> LENGTH: 7
<212> TYPE: PRT
<213> ORGANISM: Artificial sequence
<220> FEATURE:
<223> OTHER INFORMATION: Derived from avian influenza virus H9N2

<400> SEQUENCE: 7

Ile Leu Gly Tyr Lys Val Gly
1               5

<210> SEQ ID NO 8
<211> LENGTH: 7
<212> TYPE: PRT
<213> ORGANISM: Artificial sequence
<220> FEATURE:
<223> OTHER INFORMATION: Derived from avian influenza virus H9N2

<400> SEQUENCE: 8

His Pro Gln Phe Leu Ser Leu
1               5

<210> SEQ ID NO 9
<211> LENGTH: 7
<212> TYPE: PRT
<213> ORGANISM: Artificial sequence
<220> FEATURE:
<223> OTHER INFORMATION: Derived from avian influenza virus H9N2

<400> SEQUENCE: 9

Gly Leu Tyr Asn His Pro Gln
1               5
```

```
<210> SEQ ID NO 10
<211> LENGTH: 9
<212> TYPE: PRT
<213> ORGANISM: artificial sequence
<220> FEATURE:
<223> OTHER INFORMATION: Derived from avian influenza virus H9N2

<400> SEQUENCE: 10

Cys Ser Trp Gly Glu Tyr Asp Met Cys
1               5
```